(12) United States Patent
Doraiswamy et al.

(10) Patent No.: US 8,758,435 B2
(45) Date of Patent: *Jun. 24, 2014

(54) INTRAOCULAR LENS

(75) Inventors: Anand Doraiswamy, Goleta, CA (US); Jensen Buck, Goleta, CA (US); Daniel Hamilton, Napa, CA (US)

(73) Assignee: Santen Pharmaceutical Co., Ltd., Osaka (JP)

( * ) Notice: Subject to any disclaimer, the term of this patent is extended or adjusted under 35 U.S.C. 154(b) by 51 days.

This patent is subject to a terminal disclaimer.

(21) Appl. No.: 12/955,654

(22) Filed: Nov. 29, 2010

(65) Prior Publication Data

US 2012/0130488 A1 May 24, 2012

Related U.S. Application Data

(63) Continuation of application No. 12/954,424, filed on Nov. 24, 2010.

(51) Int. Cl.
*A61F 2/16* (2006.01)
(52) U.S. Cl.
USPC ........ 623/6.43; 623/6.37; 623/6.46; 623/6.49
(58) Field of Classification Search
USPC .............................. 623/6.38–6.55, 6.16–6.17
See application file for complete search history.

(56) References Cited

U.S. PATENT DOCUMENTS

| | | | |
|---|---|---|---|
| 4,254,509 A * | 3/1981 | Tennant .................. | 623/6.37 |
| 4,402,579 A * | 9/1983 | Poler .................. | 351/159.02 |
| 4,806,382 A | 2/1989 | Goldberg et al. | |
| 4,813,956 A | 3/1989 | Gupta | |
| 4,923,468 A | 5/1990 | Wild | |
| 4,969,897 A | 11/1990 | Kalb | |
| 5,049,156 A | 9/1991 | Higashi et al. | |
| 5,476,514 A * | 12/1995 | Cumming .................. | 623/6.37 |
| 5,716,403 A | 2/1998 | Tran et al. | |
| 6,179,870 B1 | 1/2001 | Sourdille et al. | |
| 6,197,059 B1 * | 3/2001 | Cumming .................. | 623/6.39 |
| D685,477 S | 7/2013 | Doraiswamy et al. | |
| D688,800 S | 8/2013 | Doraiswamy et al. | |
| D688,801 S | 8/2013 | Doraiswamy et al. | |
| D689,611 S | 9/2013 | Doraiswamy et al. | |
| D691,273 S | 10/2013 | Doraiswamy et al. | |
| 2002/0107568 A1 * | 8/2002 | Zadno-Azizi et al. ....... | 623/6.37 |
| 2003/0204257 A1 | 10/2003 | Southard | |
| 2005/0015143 A1 | 1/2005 | Willis et al. | |

(Continued)

FOREIGN PATENT DOCUMENTS

| | | |
|---|---|---|
| EP | 0 438 043 | 7/1991 |
| EP | 1457170 A1 | 9/2004 |
| WO | WO/2005/055875 A2 | 6/2005 |

OTHER PUBLICATIONS

Invitation to Pay Additional Fees, including Partial Int'l Search, for Int'l Application No. PCT/US2011/058971, Jan. 27, 2012.

(Continued)

*Primary Examiner* — Paul Prebilic
(74) *Attorney, Agent, or Firm* — Squire Sanders (US) LLP

(57) ABSTRACT

An intraocular lens comprises an optic and at least two haptics. Each haptic is offset in an anterior direction from a central optic plane of the optic. The offset allows for predictable posterior vaulting upon implantation.

16 Claims, 5 Drawing Sheets

(56) References Cited

U.S. PATENT DOCUMENTS

| | | | |
|---|---|---|---|
| 2005/0125056 A1* | 6/2005 | Deacon et al. | 623/6.21 |
| 2006/0064162 A1 | 3/2006 | Klima | |
| 2007/0100444 A1* | 5/2007 | Brady et al. | 623/6.37 |
| 2008/0109077 A1 | 5/2008 | Bos | |
| 2009/0030514 A1* | 1/2009 | Niwa et al. | 623/6.54 |
| 2009/0228102 A1* | 9/2009 | Pynson | 623/6.38 |

OTHER PUBLICATIONS

Int'l Search Report and Written Opinion, for Int'l Application No. PCT/US2011/058971, Jun. 6, 2012.

U.S. Appl. No. 29/460,792, filed Jul. 15, 2013, Anand Doraiswamy et al.

U.S. Appl. No. 29/460,805, filed Jul. 15, 2013, Anand Doraiswamy et al.

U.S. Appl. No. 29/464,872, filed Aug. 21, 2013, Anand Doraiswamy et al.

* cited by examiner

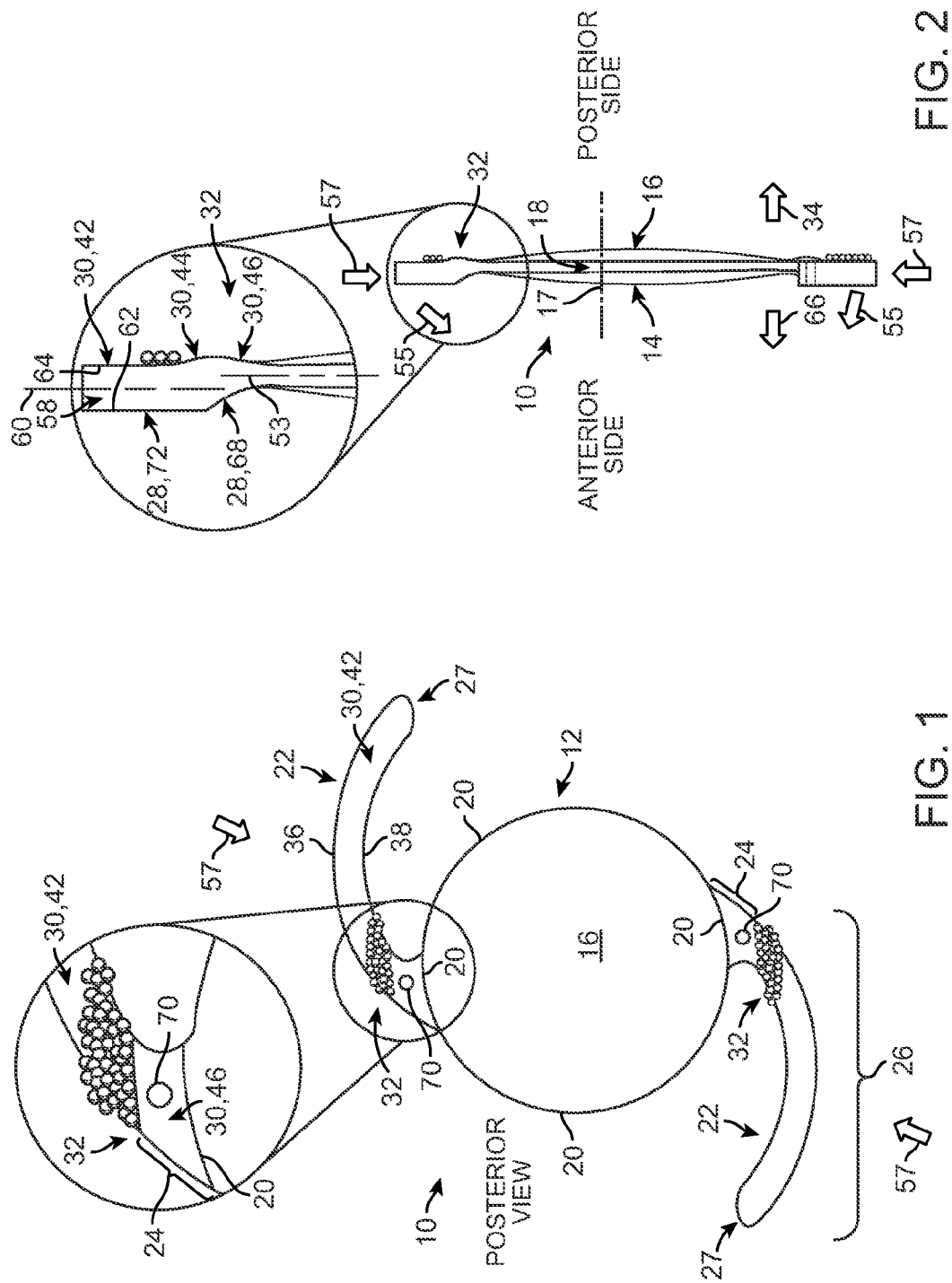

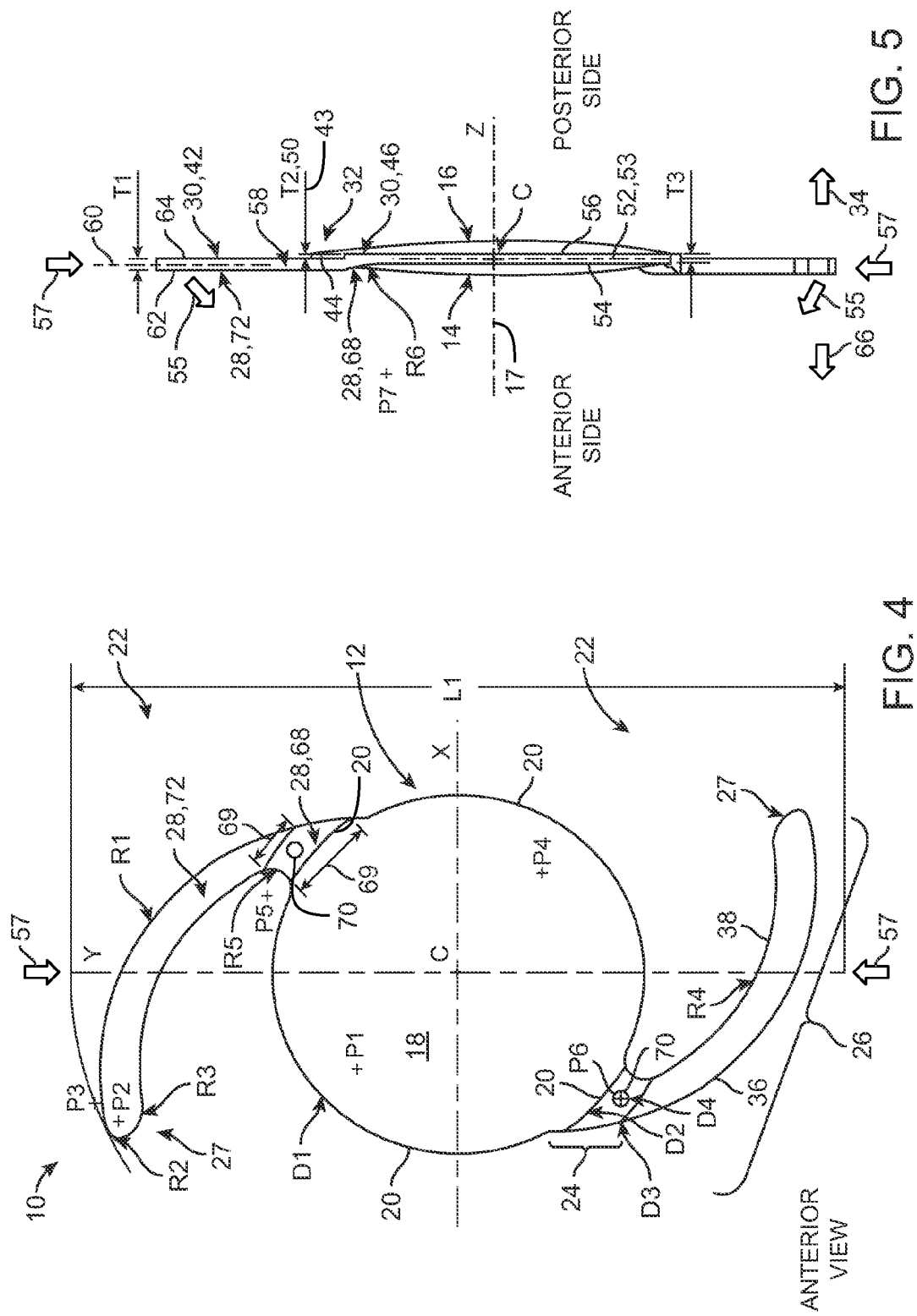

INTRAOCULAR LENS

CROSS-REFERENCE TO RELATED APPLICATION

This is a continuation of application Ser. No. 12/954,424, filed Nov. 24, 2010, which is incorporated herein by reference.

FIELD OF THE INVENTION

The invention relates generally to an intraocular lens and, more particularly, to an intraocular lens configured for implantation by minimally invasive surgery.

BACKGROUND

After implantation of an intraocular lens in the eye, epithelial cells may migrate from the haptic to the refractive region of the lens and thereby obscure the lens. This condition is known as posterior capsular opacification (PCO). Also, the refractive region of an intraocular lens may vault or push forwardly (i.e., anteriorly) in the eye when the haptic is radially compressed, such as may occur as the haptic is being seated within the capsular bag of the eye and/or when an external force is applied to the eye after implantation. Upon implantation, predictable posterior vaulting allows the final position of the lens to be more predictable thus leading to a better prediction of emmetropia. There is a continuing need to prevent PCO and make the final position of the lens more predictable.

SUMMARY OF THE INVENTION

Briefly and in general terms, the present invention is directed to an intraocular lens. In aspects of the present invention, an intraocular lens comprises an optic being substantially circular and having an optic anterior surface, an optic posterior surface, and an optic edge surface at a periphery of the optic, the optic edge surface connecting the optic anterior surface and the optic posterior surface, and at least two haptics, each haptic having a shoulder segment coupled to the periphery of the optic, an arm segment extending out from the shoulder segment, a haptic anterior surface, and a haptic posterior surface, wherein a central optic plane divides the optic edge surface into an anterior optic edge surface and a posterior optic edge surface that is substantially equal in area to the anterior optic edge surface, wherein a central optic plane divides the optic edge surface in half, wherein a central haptic plane divides the arm segment in half, and the central haptic plane is spaced apart in an anterior direction from the central optic plane.

BRIEF DESCRIPTION OF THE FIGURES

FIG. 1 is a posterior plan view of an intraocular lens according to an embodiment of the present invention, showing an optic and two haptics having a step feature that prevents epithelial cell migration to the optic.

FIG. 2 is a side view of the intraocular lens of FIG. 1, showing a central optic plane passing through an arm, segment of the haptics.

FIG. 4 is an anterior plan view of an intraocular lens according to another embodiment of the present invention.

FIG. 5 is a side view of the intraocular lens of FIG. 4, showing a central optic plane located posterior to an arm segment of the haptics.

DETAILED DESCRIPTION OF THE PREFERRED EMBODIMENTS

Figure 3:
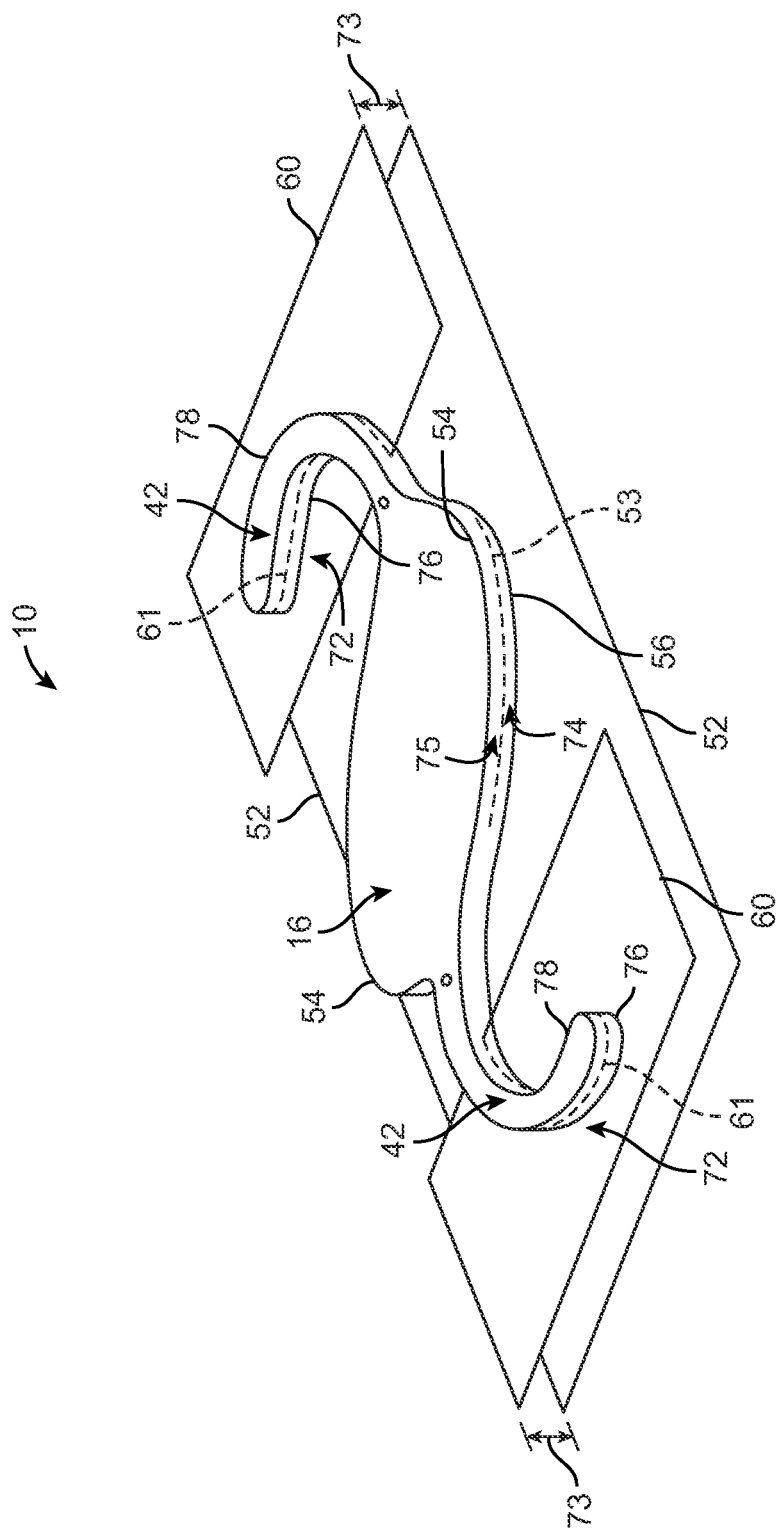
FIG. 3 is a perspective view of the intraocular lens of FIG. 1.

It is understood that with regard to this description and the appended claims, any reference to any aspect of this invention made in the singular includes the plural and vice versa unless it is expressly stated or unambiguously clear from the context that such is not intended. Thus, reference to "a" haptic or "the" haptic refers to not only one haptic but to two or more haptics unless is it unambiguously stated or unambiguously obvious from the context that such is not intended.

As used herein, any term of approximation such as, without limitation, near, about, approximately, substantially, essentially and the like mean that the word or phrase modified by the term of approximation need not be exactly that which is written but may vary from that written description to some extent. The extent to which the description may vary will depend on how great a change can be instituted and have one of ordinary skill in the art recognize the modified version as still having the properties, characteristics and capabilities of the modified word or phrase. For example without limitation, something that is described as "substantially circular" in shape refers to a shape that is perfectly circular and a shape that one skilled in the art would readily recognize as being circular even though diameters measured at multiple locations on the circle are not exactly the same. As another non-limiting example, a first structure that is described as "substantially parallel" in reference to a second structure encompasses an orientation that is perfectly parallel and an orientation that one skilled in the art would readily recognize as being parallel even though distances between corresponding locations on the two respective structures are not exactly the same. In general, but with the preceding discussion in mind, a numerical value herein that is modified by a word of approximation may vary from the stated value by ±15%, unless expressly stated otherwise.

As used herein, the terms "preferred," "preferably," and the like refer to preferences as they existed at the time of filing this patent application.

As used herein, an intraocular lens or IOL refers to a light-bending lens that is surgically placed within the eye as a replacement for the natural lens of the eye (pseudophakic lens) or as an adjunct to the image focusing property the natural lens (phakic lens), in either case for the purpose of improving the vision of—or in some cases returning vision to—a patient in whose eye the IOL is implanted.

As used herein the terms "anterior" and "posterior" refer to the spatial relationship of the construct once it is implanted in the eye. Thus, an anterior surface of an IOL faces the external environment. A posterior surface of an IOL faces the retina.

As used herein, a "leading edge" of a construct, such as a haptic, refers to the edge with the larger radius of curvature while, conversely, a "trailing edge" refers to the edge with the smaller radius of curvature.

As used herein, a "refractive region" of an IOL herein refers to that portion of the lens that performs the function of focusing or assisting in focusing an image on the retina of the eye.

As used herein, a "haptic" refers to one or more extensions extending outward from the coupling region where they act as struts to support the IOL in the capsular bag. The coupling region refers to an annular segment region at the periphery of the refractive region. Haptics are known with many different designs such as, without limitation, single piece, multi-piece, plate, closed loop and open loop. For the purposes of this invention a haptic comprises a single piece open-loop design.

As used herein, a "through hole" refers to a lumen that extends from one surface of a structure completely through the structure to another surface of the structure such that, if desired, a fluid could pass completely through the structure.

As used herein, an "exterior angle" between two constructs refers to an angle outside of the two constructs, such angle capable of being measured along an arc that runs external to the two constructs, from one construct to the other.

As used herein, a "barrier angle" refers to an exterior angle between a posterior arm surface of a haptic and a step surface intersecting the posterior arm surface, the angle being sufficient to prevent epithelial cells from migrating past the step surface.

As used herein, an "optical axis" refers to an imaginary straight line passing through the geometric center of the refractive region of an IOL and joining the two centers of curvature of the anterior and posterior surfaces of the refractive region.

Referring now in more detail to the exemplary drawings for purposes of illustrating embodiments of the invention, wherein like reference numerals designate corresponding elements among the several views, there is shown in FIGS. 1-6 an intraocular lens 10. Intraocular lens 10 is preferably made of an elastic polymer that allows it to be folded for capsular bag implantation by minimally invasive surgical methods and to unfold, either autonomously or through further manipulation, once implanted. Intraocular lens 10 comprises optic 12 that is substantially circular and serves as the refractive region of the lens. Optic 12 comprises optic anterior surface 14, optic posterior surface 16, and optic edge surface 18 at periphery 20 of the optic. Optic anterior surface 14 can have a spherical radius and optic posterior surface 16 can have an aspheric radius. The optic anterior and posterior surfaces may also be defined as either spherical, aspheric, toric, or a custom profile to correct inherent corneal aberrations, or a combination of the above. Optical axis 17 (FIGS. 2 and 5) passes through the centers of curvature of anterior surface 14 and optic posterior surface 16. Optic edge surface 18 connects optic anterior surface 14 and optic posterior surface 16. Optic edge surface 18 can have a rough texture to minimize glare.

Intraocular lens 10 further comprises at least two haptics 22. Each haptic 22 has shoulder segment 24 coupled to optic periphery 20, and arm segment 26 extending out from shoulder segment 24. Each haptic 22 terminates at free end 27 of arm segment 26. Haptics 22 are of an open C-loop design although other open loop designs can be accommodated and are within the scope of this invention. Each haptic 22 also has haptic anterior surface 28 and haptic posterior surface 30 on opposite sides of shoulder segment 24 and arm segment 26. It is understood that haptics 22 of this embodiment are presently preferred to be symmetrical so that any dimension and any feature shown for one haptic is the same for the other haptic even though it may not be expressly shown as such in the figures. It is, however, within the scope of the present invention for haptics to be asymmetrical so that a dimension or feature for one haptic is absent from the other haptic or is not the same as a corresponding feature or dimension for the other haptic.

Haptic posterior surface 30 comprises step feature 32 at shoulder segment 24. After implantation in a patient's eye, epithelial cells may attach to arm segment 26, but step feature 32 provides a barrier to prevent the cells from migrating onto the refractive region of the lens. In FIGS. 1 and 2, the epithelial cells are illustrated as small spheres on the posterior side of arm segments 26.

In a presently preferred embodiment, step feature 32 is a geometric discontinuity, such as a ledge, ridge or a bump, that is spaced apart from optic periphery 20. Step feature 32 extends continuously across shoulder segment 24 from leading edge 36 to trailing edge 38.

As shown in FIGS. 2 and 5, haptic posterior surface 30 comprises posterior arm surface 42 extending across arm segment 26. Step feature 32 protrudes in the posterior direction 34 from posterior arm surface 42, so as to form a barrier in the form of step surface 44. Step surface 44 intersects posterior arm surface 42 at a barrier angle A greater than zero. Barrier angle A can be from about 5 degrees to about 175 degrees, from about 5 degrees to about 90 degrees, or from about 90 degrees to about 175 degrees. In a presently preferred embodiments, barrier angle A is from about 80 degrees to about 110 degrees, and more narrowly at about 90 degrees. Having barrier angle A at less than 90 degrees results in an undercut, wherein step surface 44 is tilted to a position above a portion of posterior arm surface 42. In FIG. 2, barrier angle A is about 135 degrees. In FIG. 5, barrier angle A is substantially 90 degrees so that step surface 44 is substantially perpendicular to posterior arm surface 42.

Step feature 32 causes various parts of haptic posterior surface 30 to be uneven in elevation. Haptic posterior surface 30 includes posterior shoulder surface 46 that extends across shoulder segment 24. As shown in FIG. 2, posterior shoulder surface 46 is substantially planar and is uneven with the remainder of haptic posterior surface 30.

Figure 6:
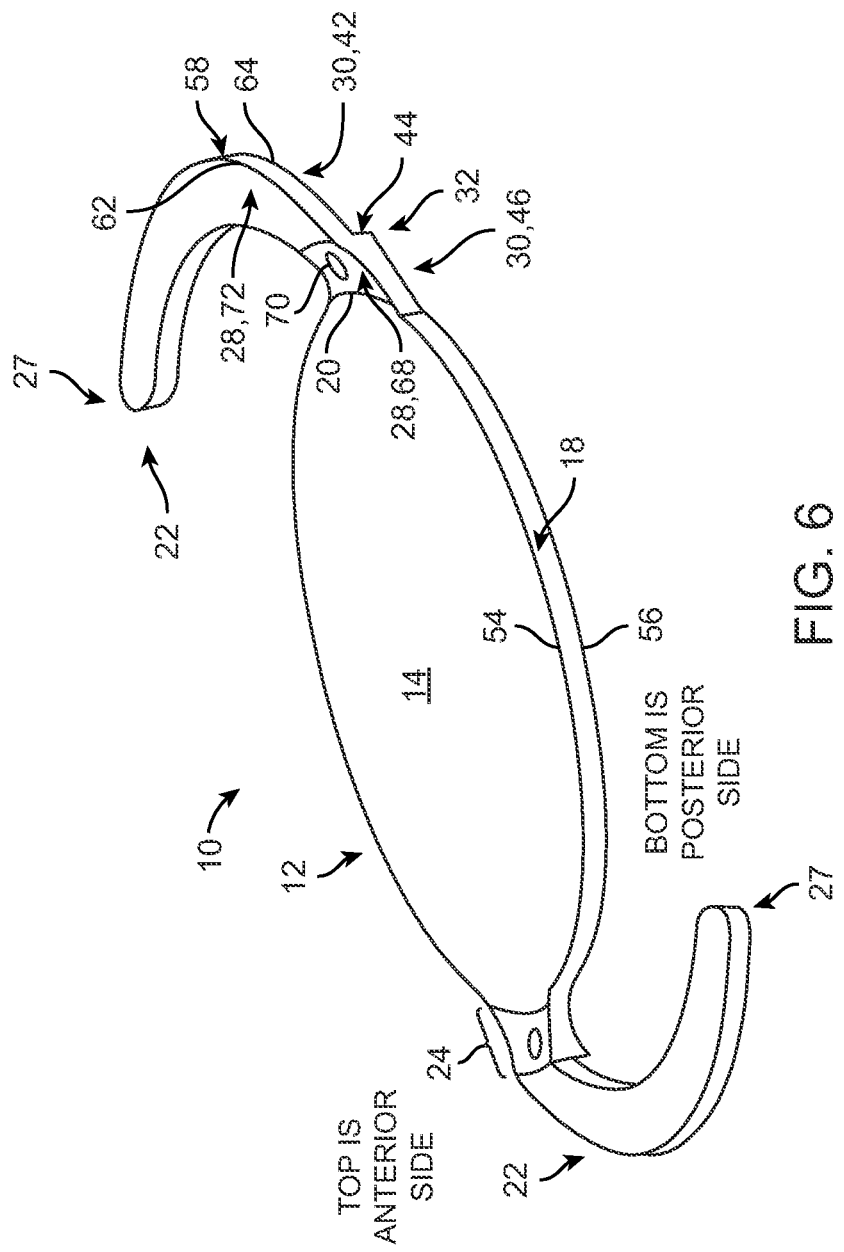
FIG. 6 is a perspective view of the intraocular lens of FIG. 4.

In the embodiment of FIGS. 4-6, posterior shoulder surface 46 and posterior arm surface 42 are substantially planar, are substantially parallel to each other, and are spaced apart from each other by a distance from 0.05 mm to 0.50 mm along an imaginary straight line 43 that is parallel to the optical axis 17. More narrowly, the distance is about 0.10 mm. The distance is the height of step feature 32 and is selected to prevent migration of epithelial cells to the refractive region of the lens.

Intraocular lens 10 may have, in combination with the step feature 32, features which addresses vaulting as described below.

In the embodiment of FIGS. 4-6, posterior shoulder surface 46 and posterior arm surface 42 are located on opposite sides of central optic plane 52 which is disposed centrally between curved anterior edge 54 of optic edge surface 18 and curved posterior edge 56 of optic edge surface 18. Central optic plane 52 passes through shoulder segment 24. The entire arm segment 26 is anterior to central optic plane 52, so central optic plane 52 does not pass through arm segment 26. Having arm segments 26 located anterior to central optic plane 52 causes arm segments 26 to bend in an anterior direction as shown by arrows 55 (FIG. 5) when radial compressive forces 57 (FIGS. 4 and 5) are applied to arm segments 26. The anterior (or forward) bend of arm segments 26 biases or tends to push optic 12 in the opposite direction, in the posterior (or rearward) direction 34, which prevents or minimizes anterior vaulting of optic 12.

In the embodiment of FIGS. 1 and 2, the entire arm segment 26 is not anterior to the central optic plane 52. Central optic plane 52 passes through arm segment 26 and shoulder segment 24. Each haptic 22 has haptic edge surface 58 connecting haptic anterior surface 28 and haptic posterior surface 30. As shown in FIG. 2, central haptic plane 60 is disposed centrally within arm segment 26 and between curved anterior edge 62 of haptic edge surface 58 and curved posterior edge 64 of haptic edge surface 58. Central haptic plane 60 is offset in an anterior direction 66 from central optic plane 52. Having central haptic plane 60 located anterior to central optic plane 52 causes the optic 12 to shift in the posterior direction when radial compressive forces 57 (FIGS. 1 and 2) are applied to arm segments 26 after implantation.

In a presently preferred embodiment, central optic plane 52 is centered between anterior edge 54 of optic edge surface 18 and posterior edge 56 of optic edge surface 18. Broken line 53 (FIG. 3) on optic edge surface 18 indicates where central optic plane 52 intersects optic edge surface 18. Central haptic plane 60 is centered between anterior arm surface 72 and posterior arm surface 42. Broken line 61 (FIG. 3) on haptic edge surface 58 indicates where central haptic plane 60 intersects haptic edge surface 58. Central optic plane 52 intersects haptic edge surface 58 below broken line 61. Central haptic plane 60 is substantially parallel to central optic plane 52 and is spaced apart in the anterior direction 66 from central optic plane 52 and are spaced apart from each other by plane-to-plane offset distance 73.

In some embodiments, as shown in FIG. 3, central optic plane 52 divides optic edge surface 18 in two halves, as anterior optic edge surface 74 and posterior optic edge surface 75 substantially equal in area to anterior optic edge surface 74. Central haptic plane 60 divides arm segment 26 in two halves, as anterior arm volume 76 and posterior arm volume 78 substantially equal in volume to anterior arm volume 76.

In some embodiments, for multiple points on central optic plane 52, each point is substantially equidistant from anterior edge 54 and posterior edge 56. For multiple points on central haptic plane 60, each point is substantially equidistant from anterior arm surface 72 and posterior arm surface 42.

Figure 7:
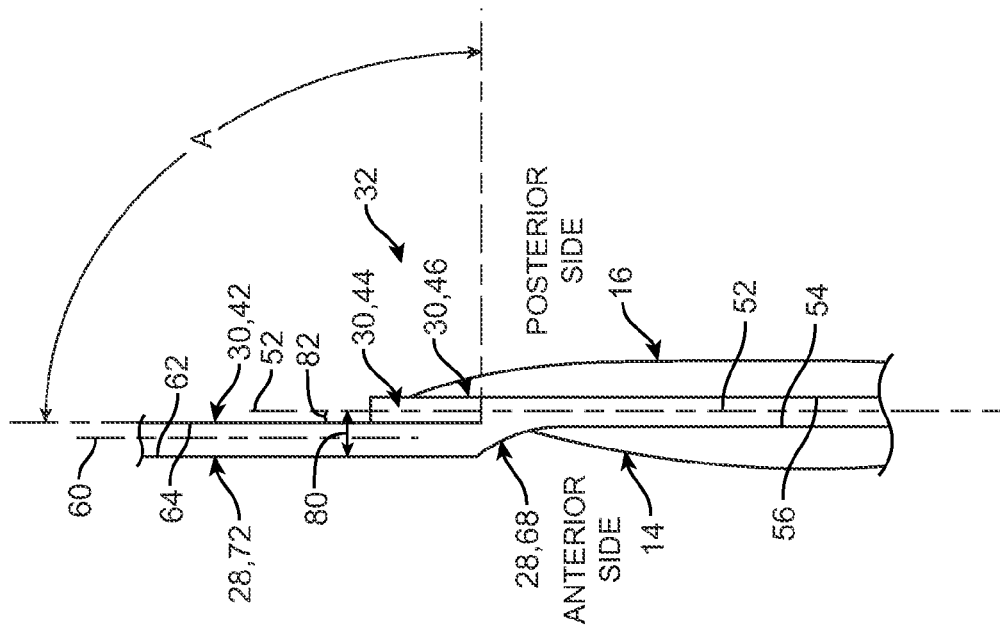
FIG. 7 is a detail side view showing the optic-haptic junction of the intraocular lens of FIG. 1.
Figure 8:
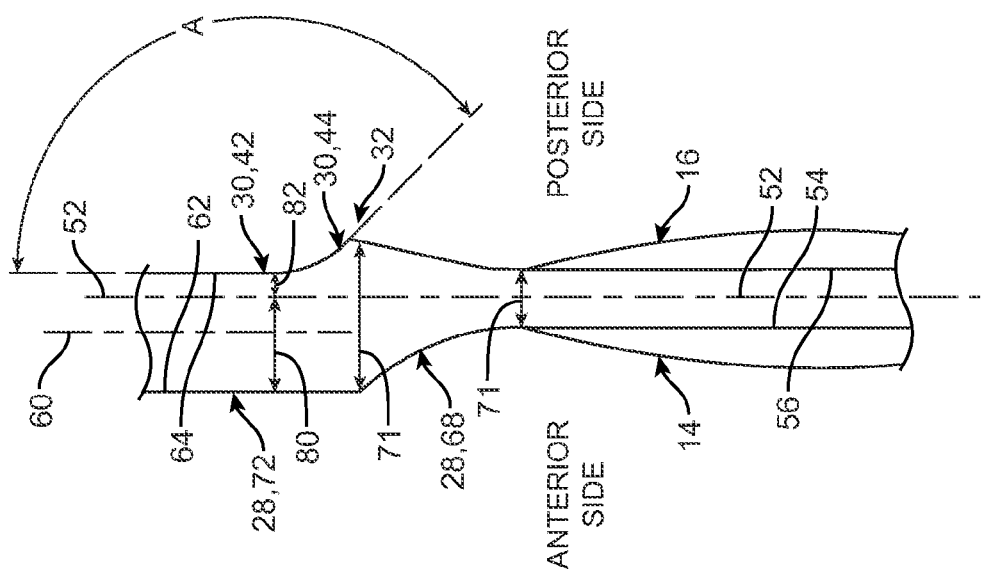
FIG. 8 is a detail side view showing the optic-haptic junction of the intraocular lens of FIG. 4.

FIG. 7 is a partial detailed view of FIG. 2. As shown in FIG. 7, anterior arm surface 72 is located entirely anterior to central optic plane 52 while posterior arm surface 42 is located entirely posterior to central optic plane 52. FIG. 8 is a partial detailed view of FIG. 5. As shown in FIG. 8, both anterior arm surface 72 and posterior arm surface 42 are located entirely anterior to central optic plane 52. In both FIGS. 7 and 8, anterior arm surface 72 is spaced apart from central optic plane 52 by first offset distance 80 as measured on a line substantially parallel to optical axis 17 (FIGS. 2 and 4). Posterior arm surface 42 is spaced apart from central optic plane 52 by second offset distance 82 on a line substantially parallel to optical axis 17. Second offset distance 82 is less than first offset distance 80, which causes arm segment 26 to bend in an anterior direction when radial compressive forces are applied to arm segment 26. This bending, in turn, causes predictable posterior displacement of optic 12 when implanted in the capsular bag of the eye.

Intraocular lens 10 may have, in combination with step feature 32 and vaulting features, another feature which facilitates bending of the haptic 22 at shoulder segment 24, such as shown in the embodiment of FIGS. 1-3 and 7 and the embodiment of FIGS. 4-6 and 8. Haptic anterior surface 28 comprises taper surface 68 that extends across the shoulder segment 24. The shoulder segment 24 has through hole 70 that runs from haptic posterior surface 30 to taper surface 68. Through hole 70 allows haptic 22 to bend at shoulder segment 24 when radial compressive forces 57 are present, without resulting in astigmatic distortions on optic 12. Through hole 70 may be circular in cross-section as illustrated, or it may have virtually any geometrical shape such as elliptical, square, rhomboid, quadrilateral, regular or irregular polygonal or simply irregularly shaped. Posterior shoulder surface 46 extends across shoulder segment 24 and connects optic periphery 20 and step feature 32. Posterior shoulder surface 46 is opposite taper surface 68, so through hole 70 extends from posterior shoulder surface 46 to taper surface 68.

As shown in FIG. 4, taper surface 68 has cross dimension 69 that narrows with increasing radial distance from optic periphery 20. Cross dimension 69 is at a maximum at optic periphery 20. The taper surface 68 intersects and ends at anterior arm surface 72. Cross dimension 69 is at a minimum where taper surface 68 intersects anterior arm surface 72. Taper surface 68 is uneven with anterior arm surface 72 in such a way that thickness 71 (FIG. 7) of shoulder segment 24 is at a minimum at optic periphery 20 and is at a maximum where taper surface 68 intersects anterior arm surface 72. The decrease in thickness 71 of haptic 22 toward optic periphery 20 facilitates anterior bending of haptic 22 along arrow 55.

The surfaces and edges of intraocular lens 10 are defined by various dimensional parameters, such as diameters (D), radii (R), lengths (L), and thicknesses (T). Dimensional parameters are labeled in FIGS. 4 and 5 with a letter followed by a number. For example, D1 and D2 refer to a first diameter and a second diameter. Diameters D1 through D3 have a common center point, C, at the center of optic 12. R1 and R2 refer to a first radius and a second radius. Each radius, R, is centered or measured out from a corresponding point, P, located according to orthogonal X-, Y- and Z-axes centered at center point C. The Z-axis corresponds to optical axis 17 of optic 12. For example, R1 and R2 refer to radii centered or measured out from points P1 and P2. Diameter D4 for through hole 70 is centered at point P6. The approximate location of each point, P, is indicated by the symbol "+" in FIGS. 4 and 5.

In a presently preferred embodiment, values for the dimensional parameters (D, R, L and T) and locations for various points (P) are as shown in TABLES 1 and 2, although other values can be accommodated and are within the scope of this invention. The locations or coordinates for various points (P) are measured from center point C. The haptics on the intraocular lens 10 is rotationally symmetric about the Z-axis passing through center point C. Dimensional parameters and point locations given for one haptic 22 apply accordingly to the opposite haptic 22. The degree of rotational symmetry is 180 degrees, such that the two haptics 22 trade positions upon rotation of 180 degrees.

TABLE 1

| Parameter | Preferred Dimension Range (mm) | Ideal Dimension (mm) |
| --- | --- | --- |
| D1 | 4.50 to 7.50 | 6.00 |
| D2 | D1+ (0 to 0.40) | D1+ 0.20 |
| D3 | D1+ (0 to 2.00) | D1+ 1.00 |
| D4 | 0.10 to 0.50 | 0.37 |
| L1 | 10.00 to 14.00 | 12.50 |
| R1 | 4.00 to 4.40 | 4.23 |
| R2 | 0.15 to 0.25 | 0.19 |
| R3 | 0.70 to 0.75 | 0.74 |
| R4 | 3.50 to 3.75 | 3.62 |
| R5 | 0.30 to 0.35 | 0.33 |
| R6 | 0.50 to 1.00 | 0.75 |
| T1 | 0.10 to 0.50 | 0.45 |
| T2 | 0 to 0.40 | 0.10 |
| T3 | 0.10 to 0.50 | 0.20 |

TABLE 2

| Point | X Coordinate (mm) | Y Coordinate (mm) | Z Coordinate (mm) |
| --- | --- | --- | --- |
| P1 | −1.524 | 1.524 | — |
| P1 | −2.575 | 5.480 | — |
| P3 | −2.158 | 5.833 | — |
| P4 | 1.524 | −1.524 | — |
| P5 | 1.161 | 3.205 | — |
| P6 | −2.052 | −2.647 | — |
| P7 | — | 2.211 | −1.782 |

As shown in FIG. 4, the size of optic 12 in plan view is defined by diameters D1 and D2. Most of optic periphery 20 coincides with D1. Near the optic-haptic junction, optic anterior surface 18 extends beyond diameter D1 to diameter D2. At the haptic-optic junction, diameter D2 defines optic periphery 20, which marks the start of taper surface 68. As shown in FIG. 5, taper surface 68 is concave and is defined in part by inside radius R6. Taper surface 68 is bounded in plan view by diameters D2 and D3. Taper surface 68 intersects anterior optic surface 14 at diameter D2 and intersects anterior arm surface 72 at diameter D3. As shown in FIGS. 4-6 and 8, the intersection at D3 forms a discontinuity between taper surface 68 and anterior arm surface 72. Thickness T1 corresponds to the Z-axis height of the portion of haptic edge surface 58 at arm segment 26. T1 also corresponds to the Z-axis separation between anterior edge 62 of haptic edge surface 58 and posterior edge 64 of haptic edge surface 58. Thickness T2 corresponds to the Z-axis height of step surface 44. T2 also corresponds to the Z-axis separation between posterior arm surface 42 and posterior shoulder surface 46. Thickness T3 corresponds to the Z-axis height of optic edge surface 18. T3 also corresponds to the Z-axis separation between anterior edge 54 of optic edge surface 18 and posterior edge 56 of optic edge surface 18.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed:

1. An intraocular lens comprising:
an optic being substantially circular and having an optic anterior surface, an optic posterior surface, and an optic edge surface at a periphery of the optic, the optic edge surface connecting the optic anterior surface and the optic posterior surface; and
at least two haptics, each haptic having a shoulder segment coupled to the periphery of the optic, an arm segment extending out from the shoulder segment, a haptic anterior surface, and a haptic posterior surface;
wherein a central optic plane divides the optic edge surface in half, wherein a central haptic plane divides the arm segment in half, and the central haptic plane is spaced apart in an anterior direction from the central optic plane, and
wherein a thickness of the shoulder segment increases continuously from the periphery of the optic to the arm segment of the haptic, and the thickness is measured in a direction parallel to an optical axis of the optic,
wherein the haptic anterior surface of each haptic comprises a taper surface extending across the shoulder segment, the taper surface is simultaneously curved and concave throughout the taper surface, the taper surface intersects an anterior arm surface of the arm segment, the intersection forms a discontinuity between the taper surface and the anterior arm surface, and the anterior arm surface is planar.

2. The intraocular lens of claim 1, wherein the haptic anterior surface of each haptic comprises the anterior arm surface, the haptic posterior surface of each haptic comprises a posterior arm surface, the anterior arm surface of each haptic is spaced apart from the central optic plane by a first offset distance on a line parallel to an optical axis of the optic, the posterior arm surface of each haptic is spaced apart from the central optic plane by a second offset distance on the line parallel to the optical axis, and the second offset distance is less than the first offset distance.

3. The intraocular lens of claim 2, wherein the anterior arm surface of each haptic and the posterior arm surface of each haptic are located anterior to the central optic plane.

4. The intraocular lens of claim 2, wherein the anterior arm surface of each haptic is located anterior to the central optic plane, and the posterior arm surface of each haptic is located posterior to the central optic plane.

5. The intraocular lens of claim 1, wherein the shoulder segment of each haptic has a through hole from the haptic posterior surface to the taper surface of the haptic anterior surface.

6. The intraocular lens of claim 1, wherein the haptic posterior surface of each haptic comprises a step feature at the shoulder segment.

7. The intraocular lens of claim 6, wherein the haptic posterior surface of each haptic comprises a posterior arm surface, and the step feature of each haptic protrudes in a posterior direction from the posterior arm surface.

8. The intraocular lens of claim 7, wherein the step feature of each haptic comprises a step surface that intersects the posterior arm surface at a barrier angle substantially greater than zero.

9. The intraocular lens of claim 8, wherein the haptic anterior surface of each haptic comprises the anterior arm surface, the anterior arm surface is spaced apart from central optic plane by a first offset distance on a line parallel to an optical axis of the optic, the posterior arm surface of each haptic is spaced apart from the central optic plane by a second offset on the line parallel to the optical axis, and the second offset is less than the first offset distance.

10. The intraocular lens of claim 1, wherein the arm segment of each haptic is planar on its anterior side.

11. The intraocular lens of claim 1, wherein the arm segment of each haptic is planar on its posterior side.

12. The intraocular lens of claim 1, wherein the increase in the thickness of the shoulder segment occurs below the taper surface.

13. The intraocular lens of claim 1, wherein the taper surface has a concave curvature having a radius centered on a point spaced apart in the anterior direction from the central optic plane.

14. The intraocular lens of claim 1, wherein the taper surface is bounded in plan view by diameter D2 and diameter D3, the taper surface intersects the optic at diameter D2, the taper surface intersects the anterior arm surface of the haptic at diameter D3, and the thickness of the shoulder segment increases continuously from diameter D2 to diameter D3.

15. The intraocular lens of claim 1, wherein the haptic anterior surface of each haptic comprises a leading edge and a trailing edge, and the taper surface extends from the leading edge to the trailing edge.

16. The intraocular lens of claim 15, wherein trailing edge includes a trailing edge segment at the taper surface, and the trailing edge segment has a concave radius centered on a point spaced radially apart from the periphery of the optic.

* * * * *